(12) United States Patent
Seneci

(10) Patent No.: US 10,149,821 B2
(45) Date of Patent: *Dec. 11, 2018

(54) OROSOLUBLE AND/OR EFFERVESCENT COMPOSITIONS CONTAINING AT LEAST A SALT OF S-ADENOSYL METHIONINE (SAME)

(76) Inventor: Alessandro Seneci, Milan (IT)

( * ) Notice: Subject to any disclaimer, the term of this patent is extended or adjusted under 35 U.S.C. 154(b) by 711 days.

This patent is subject to a terminal disclaimer.

(21) Appl. No.: 13/147,883

(22) PCT Filed: Jan. 11, 2010

(86) PCT No.: PCT/IB2010/050087
§ 371 (c)(1),
(2), (4) Date: Aug. 4, 2011

(87) PCT Pub. No.: WO2010/089674
PCT Pub. Date: Aug. 12, 2010

(65) Prior Publication Data
US 2011/0300081 A1 Dec. 8, 2011

Related U.S. Application Data

(60) Provisional application No. 61/219,553, filed on Jun. 23, 2009.

(30) Foreign Application Priority Data

Feb. 9, 2009 (IT) .............................. MI2009A0162

(51) Int. Cl.
*A61K 9/00* (2006.01)
*A61K 9/46* (2006.01)
*A61K 9/20* (2006.01)
*A61K 31/7076* (2006.01)
*A61K 47/02* (2006.01)
*A61K 47/44* (2017.01)

(52) U.S. Cl.
CPC ............ *A61K 9/0056* (2013.01); *A61K 9/006* (2013.01); *A61K 9/0007* (2013.01); *A61K 9/2009* (2013.01); *A61K 9/2018* (2013.01); *A61K 31/7076* (2013.01); *A61K 47/02* (2013.01); *A61K 47/44* (2013.01)

(58) Field of Classification Search
CPC .. A61K 9/0007; A61K 9/0056; A61K 9/2018; A61K 9/2009; A61K 9/006; A61K 31/7076; A61K 47/02; A61K 47/44
See application file for complete search history.

(56) References Cited

U.S. PATENT DOCUMENTS

| 3,954,726 A * | 5/1976 | Fiecchi | 536/27.31 |
| 4,432,975 A * | 2/1984 | Libby | A61K 33/14 514/52 |
| 6,083,531 A * | 7/2000 | Humbert-Droz | A61K 9/2095 424/435 |
| 2006/0084656 A1 * | 4/2006 | Ziegler | A61K 9/0043 514/249 |
| 2006/0127506 A1 * | 6/2006 | Hebert | 424/730 |
| 2006/0198885 A1 * | 9/2006 | Dharmadhikari | A61K 9/0056 424/464 |
| 2007/0160660 A1 * | 7/2007 | Seneci et al. | 424/451 |
| 2009/0110745 A1 * | 4/2009 | Shea | A61K 31/198 424/523 |

FOREIGN PATENT DOCUMENTS

| EP | 2193787 A1 | 9/2010 |
| WO | WO 2007/080010 A1 * | 7/2007 |

OTHER PUBLICATIONS

H.G Choi et al., "Formulation and in vivo evaluation of omeprazole buccal adhesive tablet", Journal of Controlled Release 68 (2000) 405-412.*
Sang-Chul Shin, Jin-Pil Bum and Jun-Shik Choi, "Enhanced bioavailability by buccal administration of triamcinolone acetonide from the bioadhesive gels in rabbits", International Journal of Pharmaceutics 209 (2209) 37-43.*
Nazila Salamat-Miller, Montakarn Chittchang and Thomas P. Johnston, "The use of mucoadhesive polymers in buccal drug delivery", Advanced Drug Delivery Reviews 57 (2005) 1666-1691.*
M.S. El-Samaligy, N.N. Afifi and E.A. Mahmoud, "Increasing bioavailability of silymarin using a buccal liposomal delivery system: Preparation and experimental design investigation", International Journal of Pharmaceutics 308 (2006) 140-148.*
Teodoro Bottiglieri, "S-Adenosyl-L-methionine (SAMe): from the bench to the bedside—molecular basis of a pleiotrophic molecule", The American Journal of Clinical Nutrition, 2002, 76(suppl):1151S-1157S.*
J. M. McMillan, U. K. Walle and T. Walle, "S-adenosyl-L-methionine: transcellular transport and uptake by Caco-2 cells and hepatocytes", Journal of Pharmacy and Pharmacology, 2005, 57: 599-605. (Year: 2005).*

(Continued)

*Primary Examiner* — John Pak
*Assistant Examiner* — Nathan W Schlientz
(74) *Attorney, Agent, or Firm* — Scott D. Swanson; Shaver & Swanson, LLP

(57) ABSTRACT

The present invention refers to pharmaceutical, dietary and/or nutraceutical orosoluble and/or effervescent compositions for oral use containing at least a salt of S-adenosyl methionine (SAMe), combined with physiologically acceptable excipients and optionally additional active ingredients. In particular the invention refers to compositions with high palatability formulated in tablet, capsule or granules. The present invention also refers to the use of at least a salt of SAMe combined with physiologically acceptable excipients and optionally further active ingredients for treating, human or veterinarian, neuropsychiatric, osteoarticular or hepatic diseases.

8 Claims, 2 Drawing Sheets

(56) References Cited

OTHER PUBLICATIONS

Figure 1:
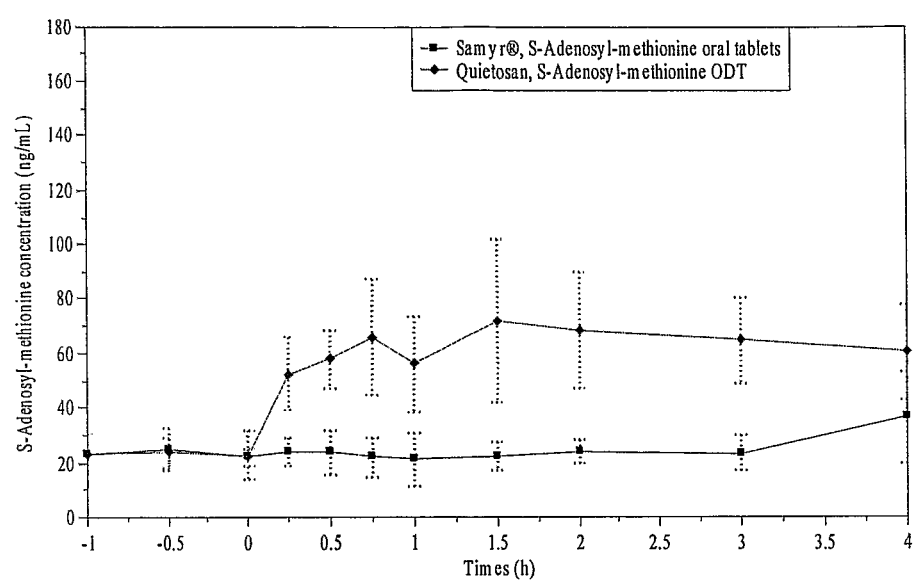

Jin Yang et al., "Pharmacokinetic Properties of S-Adenosylmethionine After Oral and Intravenous Administration of Its Tosylate Disulfate Salt: A Multiple-Dose, Open-Label, Parallel-Group Study in Healthy Chinese Volunteers", Clinical Therapeutics, 2009, 31(2), 311-320. (Year: 2009).*

Guo T, Chang L, Xiao Y, Liu Q, "S-Adenosyl-L-Methionine for the Treatment of Chronic Liver Disease: A Systematic Review and Meta-Analysis", PLoS One 2015, 10(3), 1-17. (Year: 2015).*

* cited by examiner

OROSOLUBLE AND/OR EFFERVESCENT COMPOSITIONS CONTAINING AT LEAST A SALT OF S-ADENOSYL METHIONINE (SAME)

S-adenosyl methionine (SAMe) is an important physiological molecule discovered in 1952 which is formed in the body from the combination of the methionine essential amino acid with adenosine triphosphate (ATP), in a highly demanding reaction as far as energy consumption is concerned, controlled by the SAMe synthetase enzyme.

The main natural source of SAMe for human beings is through intake of food with high protein content of its methionine precursor. It is calculated that a person under normoprotein diet averagely ingests about 1 gram of methionine to be converted into SAMe per day.

The half-life of SAMe in the liver is very short (about 5 minutes) which demonstrates the avidity of the organ for this molecule.

A good and balanced nutrition represents the key factor to supply the body with the required daily bioavailability of SAMe which may be assumed to be about 500 mg and plasma levels between 20 and 50 mg/ml (Bottiglieri T.:SAMe: from the bench to the beside-molecular basis of a pleiotropic molecule. Am. J. Clin. Nutr., 2002, 76:1151 S-1157S).

The most known deficiency conditions are for example represented by senescence wherein there occurs a drop of SAMe exceeding 50%, neurological diseases which involve the emotional sphere (depression syndromes in general) and cognitive sphere (dementia), both acute and chronic hepatic disorders (alcoholic steatosis, acute and chronic hepatitis, alcoholic and post-viral cirrhosis, intrahepatic cholestasis) and by degenerative skeletal-muscular diseases distinguished by mobility disorders (osteoarthrosis) (Grazi S., Costa M.:SAMe: The safe and natural way to combat depression and relieve the pain of osteoarthritis. Prima Health, Rocklin, Calif., 1999).

Supplementation with exogenous SAMe follows the same metabolic path as the natural molecule derived from nutritional methionine.

The idea of administering exogenous SAMe to patients was pursued since the discovery of the molecule in the fifties, but it was only after the second half of the seventies that it was put into practice with the introduction into the pharmaceutical market of the first preparations, administered parenterally (both endovenous and intramuscular) or orally (swallowable, either gastro-protected or gastro-resistant tablets) of salts of SAMe (such as for example tosylate, butanedisulfonate or phytate), stable at room temperature.

In particular, U.S. Pat. No. 3,954,726 and U.S. Pat. No. 4,057,672 describe relatively stable salts of S-adenosyl methionine, i.e. up to 25° C. and 45° C., respectively. Furthermore, the U.S. Pat. No. 4,465,672 describes stable salts of S-adenosyl methionine with 5 moles of a sulfonic acid with pK lower than 2.5.

In brief, non-salified SAMe is very unstable at temperatures above 0° C. Alongside thermolability, the second important factor of degradation of the molecule is represented by its hygroscopicity which can be bypassed by preserving the thermostable salts of SAMe in special protection casings or freeze-drying the salt under vacuum and putting it into a vial.

The availability of stable pharmaceutical preparations based on salts of SAMe allowed carrying out several clinical trials in various therapeutic uses such as depression syndromes, dementia, hepatopathies, osteoarthrosis, fibromyalgia, with the observation of proven clinical effectiveness combined with high tolerance to the molecule (Friedel H A, Goa K L, Benfield P.:SAMe: A review of its therapeutic potential in liver dysfunction and affective disorders in relation to its physiological role in cell metabolism. Drugs, 1989, 38:389-416).

After being first used in Italy, the use of SAMe in the pharmaceutical industry spread into other countries such as Spain, Germany, Russia, and China in the 80s-90s.

Lastly, starting from 1999 SAMe, salified with tosylate or butanedisulfonate, was introduced in the USA as a food supplement still in form of gastro-protected swallowable tablets dosed at 200 and 400 mg of active ingredient.

While parenteral administration (i.e. endovenous or intramuscular) of exogenous SAMe guarantees high levels of plasma bioavailability (corresponding to about 90-100% of the administered dose), oral intake of SAMe through swallowable gastro-protected tablets only produces low plasma levels of the non-modified molecule i.e. <5-10% of the administered dose.

This considerable bioavailability difference derives from the high presystemic metabolism at the hepatic level of the SAMe taken orally in gastro-protected form (i.e. gastro-resistant, capable of passing unaltered through the gastric environment and dissolving solely at the intestinal level, tributary of the portal vein).

As a matter of fact, it is known that oral intake of SAMe, radiolabeled on the carbon of the methyl group, leads to an intensive hepatic metabolism assessable at about 60% of the administered radioactivity (Giulidori P. et al.—Metabolism of exogenous SAMe in humans and its significance in the therapeutic use of the drug. Proceedings of the Workshop "*Methionine Metabolism: Molecular Mechanisms and Clinical Implications*". Madrid, Spain, Jarpyo Editores, 1998:159-163).

The high presystemic metabolism in the liver depends on the selective absorption of the SAMe at enteric level, due to the gastro-protected formulation thereof suitable to facilitate direct transfer thereof to the liver through the dominating enterohepatic portal venous system.

The systemic bioavailability levels of the molecule are drastically lowered by the metabolic avidity of the liver for SAMe.

Whereas this high presystemic metabolism of the SAMe is not prejudicial in subjects suffering from hepatic diseases, on the contrary it strongly jeopardises subjects who take orally the molecule to obtain clinical benefit related to other morbid diseases, in particular subjects suffering from depression syndromes or from osteoarthrosis, in which case molecular tropism of the extrahepatic SAMe is required.

It has been demonstrated in depressed subjects that the small plasma amount of SAMe that escapes the hepatic uptake is still capable of overcoming the obstacle of the hematoencephalic barrier and accumulating in small amounts in the cephalorachidian liquid. Regarding patients suffering from osteoarthrosis, SAMe is also capable of concentrating in the synovial fluid of the joints.

Thus, though penalised by the extensive first pass effect, the gastro-protected oral SAMe reaches the elected therapeutic sites in very little amounts.

Therefore, there is the need to increase the systemic bioavailability of the SAMe and/or its salts, when administered orally, so as to make it more suitable for treating extrahepatic diseases, for example, those regarding the central nervous system or the osteoarticular system.

Now, it has been surprisingly found that it is possible to overcome the obstacle of the hepatic presystemic metabolism of the salts of SAMe, related to the current swallowable and gastro-resistant oral formulations, through formulation in specific non-gastro-resistant orosoluble and/or effervescent compositions.

Preferably, said orosoluble and/or effervescent compositions are characterised in that they have a high palatability, which guarantees easy oral administration thereof.

Through orosoluble and/or effervescent formulations, the salts of SAMe are administered and absorbed directly in the oral cavity generating a much quicker absorption and a considerably higher bioavailability with respect to the current method of administration by means of gastro-resistant tablets, considering the same dose of active ingredient.

A similar technical effect is interpretable in the light of the fact that the oral haematic system drains in the superior vena cava avoiding the portal venous system responsible for the known first pass effect, thus improving the systemic bioavailability.

Thus, the present invention refers to orosoluble and/or effervescent compositions for oral use containing at least a salt of SAMe combined with physiologically acceptable excipients.

The orosoluble and/or effervescent compositions of the invention are preferably characterised in that they have a high palatability which guarantees easy oral administration thereof.

Said high palatability also determines in the treated subject (human or animal) a greater period of permanence of the composition in the oral cavity, and an ensuing lower impulse to swallow, which contributes to improve the rate of absorption and the bioavailability of the active ingredient.

According to the present invention the term "SAMe" is used to indicate both the racemic mixture and the single diastereoisomers (RS)-(+)-S-adenosyl-L-methionine [(RS)-(+)-SAMe)] and (SS)-(+)-S-adenosyl-L-methionine [(SS)-(+)-SAMe)], even in mixtures different from the racemic one.

According to the present invention the salts of SAMe are preferably selected from among tosylate (para-toluenesulfonate), butanedisulfonate, phytate or a mixture thereof. Said at least a salt of SAMe is comprised in the compositions according to the invention in an amount ranging from 5 to 70% by weight, preferably from 7 to 50% by weight, with respect to the weight of the composition.

According to the invention, said percentage ranges refer to the total amount of the salt of SAMe, or to the total amount of the salts of SAMe in the mixture, contained in the composition.

The orosoluble and/or effervescent compositions of the invention may thus be formulated in form of tablet, capsule and/or granules, preferably in form of orosoluble and/or effervescent tablet. The compositions of the invention may also be formulated in form of sublingual tablet.

According to the invention, the term "sublingual" refers to compositions which must specifically be placed under the tongue in order to dissolve and release the active ingredient.

According to the invention the term "orosoluble" refers to a composition capable of immediately dissolving and releasing the active ingredient contained therein upon contact with the oral mucosa. In this manner, the active ingredient may be directly absorbed in the oral mucosa, thus bypassing the hepatic system.

According to the invention the term orosoluble is therefore preferably used to indicate compositions to be introduced into the oral cavity.

In order to obtain the orosoluble form, the compositions of the invention are preferably formulated using the following classes of excipients: diluents, aggregants or binding agents, lubricants, glidants, disaggregants, solubilisers, sweeteners, flavouring agents and/or pH adjusters.

More preferably, the orosoluble compositions according to the invention are formulated with light magnesium oxide, magnesium hydroxide, alginic acid, stearic acid, hydrogenated vegetable oils (palm, oleic, behenic), cocoa butter, cocoa paste, xylitol, maltitol, sorbitol, mannitol, sucralose, acesulfame K, cyclamate, aspartame, sucrose, neohesperidine, fructose, dextrose, maltose, spray dried malt, sodium aspartate, maltodextrines, inositol, inulin, chitosan, beer yeast or a mixture thereof.

In particular, in order to obtain the orosoluble form, said excipients are present in the compositions of the invention in an amount ranging from 20% to 95% by weight, with respect to the total weight of the formulation.

According to the invention, the term "effervescent" instead refers to compositions capable of developing carbon dioxide when at contact with water and/or with the buccal environment, in the presence of saliva and they are divided into:

A: slightly effervescent orosoluble tablets. Thus capable of developing slight effervescence capable of guaranteeing high palatability associated to a dissolution time within 10 minutes.

B: classic effervescent tablets. To be dissolved in water and to be taken at small sips.

In order to obtain the effervescent form, the compositions of the invention are preferably formulated using di- and tri-carboxylic acids or a mixture thereof.

More preferably, the effervescent compositions according to the invention are formulated with dihydrate and monohydrate sodium citrate, sodium carbonate, disodium carbonate, potassium bicarbonate, citric acid, tartaric acid, adipic acid, monosodium phosphate, alginic acid, magnesium hydroxycarbonate or a mixture thereof.

In particular, in order to obtain the effervescent form, said excipients are present in the compositions of the invention in an amount ranging from 30% to 95% by weight, with respect to the total weight of the formulation.

The compositions of the invention may therefore be formulated in orosoluble form, effervescent form or a combined orosoluble and effervescent form.

The term "high palatability" according to the invention refers to compositions having a particularly pleasant taste that can be easily administered orally regardless of the fact that the active ingredients contained therein may have an unpleasant, bitter and/or sour taste.

Further useful excipients according to the invention are selected from among sodium-, calcium-, magnesium-, potassium-citrate, sodium-, calcium-, magnesium-, potassium-phosphate, light magnesium oxide, magnesium hydroxide, magnesium hydroxycarbonate, sodium carbonate, sodium chloride, potassium carbonate, sodium hydrogen carbonate, potassium hydrogen carbonate, adipic acid, citric acid, tartaric acid, alginic acid, stearic acid and its salts, oleic acid, l-leucine, glycerol behenate, hydroxypropylmethylcellulose, hydrogenated vegetable oils (such as for example palm oil), palm butter, cocoa butter, cocoa paste, cocoa powder, xylitol, maltitol, sorbitol, mannitol, sucralose, acesulfame K, sodium cyclamate, aspartame, sucrose, erythritol, citrus extract, fructose, dextrose, maltose, spray dried malt, sodium aspartate, neohesperidine, maltodextrines, inositol, inulin, beer yeast, silica gel, vegetable fibres (such as for example pea fibre), chitosan, flavouring agents (essential oils, powders and the like): mint (peppermint, spearmint, sweet mint), badian anethole, vanilla, sage, liver, sodium glutamate, fish meal, chicken, grapefruit, peach, lime or a mixture thereof.

The compositions according to the present invention may also contain at least a further active ingredient in combination with said at least a salt of SAMe, maintaining the high palatability of the compositions. Said further active ingredient is preferably selected from among vitamins, amino acids, glycosaminoglycans, flavolignans, hormones, natural substances of animal or vegetable origin, enzymes, polysaccharides, probiotics or a mixture thereof.

In particular, said further active ingredient may be selected from among vitamins of group B such as, for example, vitamin B6, vitamin B12, vitamin B9 (folic acid), methylfolate, vitamin C; magnesium salts; taurine, tryptophan, reduced glutathione, n-acetylcysteine, tyrosine; hyaluronic acid, silymarin, silybin, 1-theanine, melatonin, bromelain, hypericum, lipoic acid, lycopenes, bioflavonoids, rutin, valerian, glucosamine, chondroitin sulphate, chitosan, ursodeoxycholic acid, *lactobacillus acidophilus, lactobacillus vulgaris, bifidum bacterium brevi, bifidum infantis, bifidum bacterium lactis, bifidum bacterium longum, lactobacillus bulgaricus, lactobacillus casei, lactobacillus plantarum, lactobacillus rhamnosus*; melissa, cinnamon, hawthorn, granadilla, fennel, dried garlic, onion, melaleuca, sweet orange, camomile, thyme (in form of essential oils, mother tinctures, retted glycerides or powders), betaine, aspartic acid, glutamine, phosphoserine, phosphatidylserine, choline, coenzyme Q10, dimethylglycine, hydroxymethylbutyrate, lactoferrin, methylsulfonylmethane, homotaurine, p-aminobenzoic acid (PABA), *monacus purpureus* or a mixture thereof.

Said at least an additional active ingredient is contained in the composition of the invention in an amount ranging from 0.05% to 70%, preferably from 0.1 to 55%, with respect to the total weight of the composition.

Said amount varies depending on the characteristics of the selected additional active ingredient.

In particular, in case the additional active ingredient is one of the abovementioned vitamins of group B the dose according to the invention ranges from 0.00001 to 3%, preferably from 0.00005 to 1%, with respect to the total weight of the composition.

As mentioned above, administration of the composition according to the present invention guarantees an improved bioavailability of the drug, with respect to the compositions already available in the market; as a matter of fact, the administration of the invention allows reaching the plasma peak of the SAMe ion (maximum plasma concentration) within a period of time comprised between 1 and 2 hours from intake, preferably within about 1 and a half hours, with respect to a period of time of about 5 hours observed regarding a swallowable gastro-resistant tablet available in the market.

Said plasma peak of the invention corresponds to a plasma concentration value of the SAMe ion greater than 40-50% with respect to the base value, preferably equivalent to a value higher than 48% with respect to the base value, instead of the 1% observed on a swallowable gastro-resistant tablet available in the market. Thus, the present invention is also aimed at providing a method for obtaining the plasma peak of the SAMe ion within a period of time comprised between 1 and 2 hours from the intake, preferably within a period of time of about 1 and a half hours, characterized by the intake of the composition according to the present invention.

In particular, the method of the present invention determines a plasma concentration of the SAMe ion greater than 40-50% with respect to the base value, preferably greater than a value of about 48%, with respect to the base value.

The present invention is thus aimed at providing a method for increasing the plasma concentration of the SAMe ion characterized by administering the composition of the invention.

In particular, according to the method of the invention the value of the plasma concentration of the SAMe ion increases from 30 to 40% within a period of time preferably comprised between 20 and 40 minutes after administering the abovementioned composition. More preferably, the plasma concentration value of the SAMe ion increases by about 35% after about 30 minutes from the intake of the composition of the invention.

According to the method of the invention, the plasma peak of the SAMe ion (maximum plasma concentration) is attained within a period of time comprised between 1 and 2 hours, while the plasma concentration already increases considerably after a period of time comprised between 20 and 40 minutes from intake, thus guaranteeing the fast effectiveness.

Furthermore, the present invention refers to orosoluble and/or effervescent compositions containing at least a salt of SAMe combined with physiologically acceptable excipients used for treating, human or veterinarian, neuropsychiatric, osteoarticular or hepatic diseases and/or for treating disorders or discomforts deriving from the abovementioned diseases, in particular, diseases and/or disorders regarding the emotional sphere (depression syndromes in general, anxiety) and cognitive sphere (dementia), hepatic disorders both acute and chronic (alcoholic steatosis, acute and chronic hepatitis, alcoholic and post-viral cirrhosis, intrahepatic cholestasis) and degenerative skeletal-muscular diseases distinguished by mobility disorders (osteoarthrosis).

The abovementioned compositions for use in the treatment of human or veterinarian, neuropsychiatric, osteoarticular or hepatic diseases and/or disorders or discomforts deriving from the abovementioned diseases may also contain additional active ingredients. Said additional active ingredients being preferably selected from among vitamins, amino acids, glycosaminoglycans, flavolignans, hormones, natural substances of animal or vegetable origin, enzymes, polysaccharides, probiotics.

The compositions of the present invention may be prepared through a process comprising the following steps:
Scheme a (for Orosoluble and/or Effervescent Tablets or Granules and Capsules):
1) Weighing the active components and excipients;
2) Mixing (mixer with rotating screw);
3) Compression;
4) Dry granulation of the obtained tablets;
5) Final compression or using the granules obtained in step 4 directly packaged in sachets or capsules.
Scheme B (for Orosoluble Tablets or Granules and Capsules):
 1) Weighing components except light magnesium oxide and at least a salt of SAMe;
 2) Granulation by means of a slurry with a moistening mixture made up of an aqueous solution of a binding excipient;
 3) Drying on a fluid bed until moisture below about 1% is obtained;
 4) Adjusting the granules size by means of an oscillating granulator provided with a perforated stainless steel mesh (preferably with 1.5 mm diameter holes);

5) Mixing the granules+at least a salt of SAMe+light magnesium oxide+flavouring agents;
6) Final compression or using the granules obtained in step 5 directly packaged in sachets or capsules.

Scheme C (for Orosoluble Tablets or Granules and Capsules):
1) Weighing all components;
2) Granulation by mixing with rendered vegetable fats;
3) Refrigeration and granulation of the mixture;
4) Adjusting the granules size by means of an oscillating granulator provided with a perforated stainless steel mesh (preferably with 1.5 mm diameter holes);
5) Final compression or using the granules obtained in step 4 directly packaged in sachets or capsules.

The process of the present invention is preferably performed maintaining the temperature between about 20° C. and 30° C., more preferably at about 25° C., with relative humidity preferably not exceeding 28%.

According to the abovementioned process the finished product has relative humidity preferably below 3%, more preferably below 1.5%.

The following examples represent a detailed description of the compositions of the invention without limiting the contents thereof in any way whatsoever.

EXAMPLES

Example 1

Orosoluble Tablet Based on SAMe Tosylate (Para-Toluenesulfonate)

| | |
|---|---|
| SAMe tosylate (para-toluenesulfonate) | 200 mg (equivalent to 100 mg of the SAMe ion) (13.33%) |
| Folic acid | 0.15 mg (0.010%) |
| Vitamin B12 | 0.001 mg (6.6 * $10^{-5}$ %) |
| Light magnesium oxide | 40 mg (2.67%) |
| Stearic acid | 90 mg (6%) |
| Glycerol behenate | 7 mg (0.47%) |
| Magnesium stearate | 10 mg (0.66%) |
| Mint flavour | 3.53 mg (0.24%) |
| Mixture of flavours: (Lime, Granadilla and Hawthorn) | 0.3 mg (0.020%) |
| Silica gel | 4.53 mg (0.3%) |
| Xylitol | 350 mg (23.33%) |
| Mannitol | 793 mg (52.86%) |
| Sucralose | 1.45 mg (0.1%) |
| Neohesperidin | 0.16 mg (0.010%) |
| TOTAL weight of the tablet | 1500.12 mg |

Orosoluble tablets are preferably made having a diameter of 19 mm and weighing about 1.50 g

Example 2

Orosoluble Tablet Based on SAMe Tosylate (Para-Toluenesulfonate)

| | |
|---|---|
| SAMe tosylate (para-toluenesulfonate) | 233 mg (equivalent to 119.76 mg of the SAMe ion) (10.53%) |
| Light magnesium oxide | 44 mg (2%) |
| Stearic acid | 80 mg (3.6%) |
| Glycerol behenate | 7 mg (0.3%) |
| Magnesium stearate | 10 mg (0.45%) |
| Mint flavour | 3.53 mg (0.16%) |
| Essential Melissa oil | 0.1 mg (0.007%) |
| Anethole | 0.056 mg (0.005%) |
| Silica gel | 4.53 mg (0.2%) |
| Inositol | 908 mg (41.08%) |
| Mannitol | 470.21 mg (21.25%) |
| Xylitol | 450 mg (20.34%) |
| Sucralose | 1.6 mg (0.07%) |
| Neohesperidin | 0.18 mg (0.008%) |
| TOTAL tablet weight | 2212.21 mg |

Orosoluble tablets are preferably made having a diameter of 22 mm and weighing about 2.2 g

Example 3

Orosoluble Tablet Based on SAMe Tosylate (Para-Toluenesulfonate)

| | |
|---|---|
| SAMe tosylate (para-toluenesulfonate) | 420 mg (equivalent to 200 mg of the SAMe ion) (17.87%) |
| Light magnesium oxide | 150 mg (6.38%) |
| Stearic acid | 160 mg (6.8%) |
| Glycerol behenate | 13 mg (0.55%) |
| Magnesium stearate | 20 mg (0.85%) |
| Xylitol | 859.57 mg (36.57%) |
| Mannitol | 700 mg (29.78%) |
| Sucralose | 4.5 mg (0.19%) |
| Neohesperidine | 0.3 mg (0.01%) |
| Orange flavour | 14.63 mg (0.62%) |
| Silica gel | 8 mg (0.34%) |
| TOTAL tablet weight | 2350.00 mg |

Orosoluble tablets are preferably made having a diameter of 22 mm and weighing about 2.4 g

Example 4

Effervescent Orosoluble Tablet Based on SAMe Tosylate (Para-Toluenesulfonate)

| | |
|---|---|
| SAMe tosylate (para-toluenesulfonate) | 233 mg (equivalent to 119.762 mg of the SAMe ion) (10.30%) |
| Light magnesium oxide | 20.5 mg (0.9%) |
| L-leucine | 24 mg (1.06%) |
| Glycerol behenate | 4 mg (0.18%) |
| Magnesium stearate | 1 mg (0.04%) |
| Grapefruit flavour powder | 50 mg (2.21%) |
| Inositol | 800 mg (35.36%) |
| Sucralose | 10 mg (0.44%) |
| Anhydrous disodium carbonate | 400 mg (17.68%) |
| Citric acid | 250 mg (11.05%) |
| Adipic acid | 250 mg (11.05%) |
| Sodium carbonate | 200 mg (8.85%) |
| Silica gel | 20 mg (0.88%) |
| TOTAL tablet weight | 2262.50 mg |

Tablets are preferably made having a diameter of 22 mm and weighing about 2.2 g

Example 5

Orosoluble Tablet Based on SAMe Tosylate (Para-Toluenesulfonate) (Veterinary Use

| | |
|---|---|
| SAMe tosylate (para-toluenesulfonate) | 233 mg (equivalent to 119.762 mg of the SAMe ion) (9.19%) |

-continued

| | |
|---|---|
| Light magnesium oxide | 38.5 mg (1.52%) |
| Glycerol behenate | 7 mg (0.27%) |
| Stearic acid | 80 mg (3.15%) |
| Liver flavour | 2 mg (0.08%) |
| Yeast flavour | 1 mg (0.04%) |
| Silica gel | 20 mg (0.79%) |
| Dry liver | 500 mg (19.72%) |
| Dry yeast | 1200 mg (47.32%) |
| Glucosamine sulphate | 250 mg (9.87%) |
| Monosodium glutamate | 50 mg (1.97%) |
| Sodium chloride | 20 mg (0.79%) |
| Xylitol | 134 mg (5.28%) |
| Neohesperidine | 0.2 mg (0.01%) |
| TOTAL tablet weight | 2535.70 mg |

Orosoluble tablets are preferably made having a diameter of 22 mm and weighing about 2.5 g.

Example 6

Orosoluble Tablet Based on SAMe Butanedisulfonate (Veterinary Use

| | |
|---|---|
| SAMe butanedisulfonate | 233 mg (equivalent to 119.762 mg of the SAMe ion) (10.19%) |
| Light magnesium oxide | 38.5 mg (1.68%) |
| Glycerol behenate | 7 mg (0.31%) |
| Stearic acid | 80 mg (3.5%) |
| Liver flavour | 2 mg (0.09%) |
| Yeast flavour | 1 mg (0.04%) |
| Silica gel | 20 mg (0.87%) |
| Dry liver | 500 mg (21.88%) |
| Dry yeast | 1200 mg (52.5%) |
| Monosodium glutamate | 50 mg (2.19%) |
| Sodium chloride | 20 mg (0.88%) |
| Xylitol | 134 mg (5.86%) |
| Neohesperidine | 0.2 mg (0.01%) |
| TOTAL tablet weight | 2285.70 mg |

Orosoluble tablets are preferably made having a diameter of 22 mm and weighing about 2.25 g

Example 7

Orosoluble Tablet Based on SAMe Phytate

| | |
|---|---|
| SAMe phytate | 215 mg (equivalent to 113.10 mg of the SAMe ion) (14.41%) |
| Silymarin | 100 mg (6.7%) |
| Reduced glutathione | 25 mg (1.68%) |
| Ursodeoxycholic acid | 150 mg (10.05%) |
| Light magnesium oxide | 42 mg (2.82%) |
| Palm oil | 25 mg (1.68%) |
| Maltodextrine | 200 mg (13.52%) |
| Mannitol | 700 mg (46.94%) |
| Magnesium stearate | 15 mg (1%) |
| Dextrose | 5 mg (0.33%) |
| Spray dried malt | 2.5 mg (0.17%) |
| Mixture of flavours: (thyme, mint, spearmint, *vanilla*) | 6 mg (0.4%) |
| Silica gel | 4 mg (0.20%) |
| Sucralose | 2 mg (0.10%) |
| TOTAL tablet weight | 1491.50 mg |

Orosoluble tablets are preferably made having a diameter of 19 mm and weighing about 1.5 g

Example 8

Orosoluble Tablet Based on SAMe Tosylate (Para-Toluenesulfonate)

| | |
|---|---|
| SAMe tosylate (para-toluenesulfonate) | 243 mg (equivalent to 121.5 mg of the SAMe ion) (11.61%) |
| Valerian | 150 mg (7.17%) |
| *Hypericum* | 7 mg (0.33%) |
| Tryptophan | 100 mg (4.78%) |
| Light magnesium oxide | 33 mg (1.58%) |
| Glycerol behenate | 85 mg (4.06%) |
| Magnesium stearate | 11 mg (0.52%) |
| Xylitol | 500 mg (23.90%) |
| Mannitol | 950 mg (45.40%) |
| Silica gel | 3.7 mg (0.18%) |
| Acesulfame K | 1.2 mg (0.05%) |
| Cyclamate | 0.9 mg (0.04%) |
| Mixture of flavours: (Peppermint, fennel and cinnamon) | 4.5 mg (0.21%) |
| Silica gel | 3.5 mg (0.17%) |
| TOTAL tablet weight | 2092.80 mg |

Orosoluble tablets are preferably made having a diameter of 22 mm and weighing about 2 g

Example 9

Effervescent Orosoluble Tablet Based on SAMe Tosylate (Para-Toluenesulfonate) and SAMe Butanedisulfonate

| | |
|---|---|
| SAMe tosylate (para-toluenesulfonate) | 90 mg (equivalent to 45 mg of the SAMe ion) (7.37%) |
| SAMe butanedisulfonate | 90 mg (equivalent to 45 mg of the SAMe ion) (7.37%) |
| N-acetylcysteine | 50 mg (4.09%) |
| Vitamin C | 60 mg (4.91%) |
| Bioflavonoids | 150 mg (12.29%) |
| Light magnesium oxide | 29 mg (2.37%) |
| Potassium bicarbonate | 400 mg (32.77%) |
| Tartaric acid | 230 mg (18.85%) |
| Citric acid | 50 mg (4.1%) |
| Leucine | 40 mg (3.28%) |
| Glycerol behenate | 6 mg (0.49%) |
| Magnesium stearate | 7 mg (0.57%) |
| Sodium aspartate | 3.5 mg (0.28%) |
| Maltitol | 5 mg (0.42%) |
| Mixture of flavours: (sweet mint, sage) | 5 mg (0.42%) |
| Silica gel | 5 mg (0.42%) |
| TOTAL tablet weight | 1220.50 mg |

Tablets are preferably made having a diameter 19 mm and weighing about 1.2 g

Example 10

Orosoluble Tablet Based on SAMe Butanedisulfonate

| | |
|---|---|
| SAMe butanedisulfonate | 243 mg (equivalent to 127.8 mg of the SAMe ion) (14.38%) |
| *Lactobacillus acidophilus* (150 mld) | 10 mg (0.59%) |
| *Bifidum bacterium longum* (100 mld) | 20 mg (1.18%) |
| Sodium citrate | 100 mg (5.91%) |

| -continued | |
|---|---|
| Stearic acid | 85 mg (5.22%) |
| Maize starch | 50 mg (2.95%) |
| Magnesium stearate | 14 mg (0.93%) |
| Silica gel | 4.3 mg (0.25%) |
| Inulin | 400 mg (23.65%) |
| Mannitol | 300 mg (17.74%) |
| Sucrose | 300 mg (17.74%) |
| Glycine | 151 mg (8.99%) |
| Mixture of flavours: | 3 mg (0.18%) |
| (melissa, granadilla and hawthorn) | |
| Silica gel | 4 mg (0.23%) |
| Acesulfame K | 1 mg (0.06%) |
| TOTAL tablet weight | 1691.30 mg |

Orosoluble tablets are preferably made having a diameter of 19 mm and weighing about 1.6 g

Example 11

Orosoluble Tablet Based on SAMe Tosylate (Para-Toluenesulfonate) (Sublingual)

| | |
|---|---|
| SAMe tosylate (para-toluenesulfonate) | mg (equivalent to 30.84 mg of the SAMe ion) (24.83%) |
| Melatonin | 1 mg (0.42%) |
| Light magnesium oxide | 4.8 mg (1.99%) |
| Glycerol behenate | 19 mg (7.86%) |
| Magnesium stearate | 2.5 mg (1.03%) |
| Xylitol | 95 mg (39.32%) |
| Hydroxypropylcellulose | 55 mg (22.77%) |
| Sucralose | 0.5 mg (0.21%) |
| Mixture of flavours: | 1.8 mg (0.74%) |
| (sweet orange oil and cinnamon) | |
| Silica gel | 2 mg (0.83%) |
| TOTAL tablet weight | 241.60 mg |

Sublingual tablets are preferably made weighing 0.24 g

Example 12

Effervescent Granules Based on SAMe Tosylate (Para-Toluenesulfonate)

| | |
|---|---|
| SAMe tosylate (para-toluenesulfonate) | mg (equivalent to 80 mg of the SAMe ion) (13.20%) |
| Glucosamine | 100 mg (8.25%) |
| Chondroitin sulphate | 100 mg (8.25%) |
| Hyaluronic acid | 5 mg (0.41%) |
| Light magnesium oxide | 29 mg (2.2%) |
| Potassium bicarbonate | 400 mg (33.00%) |
| Tartaric acid | 230 mg (18.98%) |
| Citric acid | 150 mg (12.37%) |
| Magnesium stearate | 4 mg (0.33%) |
| Aspartame | 4 mg (0.33%) |
| Xylitol | 20 mg (1.76%) |
| Mixture of flavours: | 5 mg (0.41%) |
| (granadilla, hawthorn and chamomile) | |
| Silica gel | 5 mg (0.41%) |
| TOTAL weight | 1212.00 mg |

Sachets are preferably made weighing about 1.2 g

Example 13

Slightly Effervescent Orosoluble Tablet Based on SAMe Tosylate (Para-Toluenesulfonate)

| | |
|---|---|
| SAMe tosylate (para-toluenesulfonate) | 400 mg (equivalent to 200 mg of the SAMe ion) (32.24%) |
| N-acetylcysteine | 50 mg (4.03%) |
| Vitamin C | 60 mg (4.83%) |
| Bioflavonoids | 150 mg (12.09%) |
| Light magnesium oxide | 29 mg (2.34%) |
| Potassium bicarbonate | 200 mg (16.12%) |
| Tartaric acid | 230 mg (18.54%) |
| Citric acid | 50 mg (4.0.3%) |
| Leucine | 40 mg (3.22%) |
| Glycerol behenate | 6 mg (0.48%) |
| Magnesium stearate | 7 mg (0.56%) |
| Sodium aspartate | 3.5 mg (0.28%) |
| Citrus extract | 5 mg (0.4%) |
| Mixture of flavours: | 5 mg (0.4%) |
| (bitter orange) | |
| Silica gel | 5 mg (0.4%) |
| TOTAL tablet weight | 1240.50 mg |

Tablets are preferably made having a diameter 19 mm and weighing about 1.2 g

EXPERIMENTAL PART

Using the formulation in the orosoluble tablet containing SAMe tosylate (para-toluenesulfonate) of example 2 (Quietosan ♦) a comparative trial was carried out to evaluate the bioavailability thereof compared to a composition formulated in swallowable gastro-resistant tablets available in the market (Samir® ■).

For such purpose, six subjects from both genders, healthy volunteers, took under fasting, in a randomised manner and crossover pattern (i.e. a pattern according to which all patients take both treatments one after the other) 119.76 mg of the SAMe ion formulated according to the invention (formula example 2) and 200 mg of the SAMe ion in the swallowable gastro-resistant tablet available in the market (Samir®).

The results obtained were normalised to take into account the concentration difference of the two pharmaceutical forms.

The plasma bioavailability, expressed as AUC, of the formulation in orosoluble tablets of SAMe tosylate according to the invention was considerably higher, averagely from about 150% to about 200% higher, with respect to the swallowable gastro-resistant one.

The concentration peak time was about one hour, one and a half hours (plasma bioavailability started increasing immediately after intake) for the orosoluble tablet of the invention and about 5 hours for the swallowable gastro-resistant one (FIG. 1).

Furthermore as shown in FIG. 1, plasma concentration after one hour-one and a half hours from the intake of the orosoluble tablet of the invention was about 48% higher than the base value, while the plasma bioavailability after one hour-one and a half hours from the intake of the swallowable gastro-resistant tablet is about 1% higher with respect to the base value.

Figure 2:
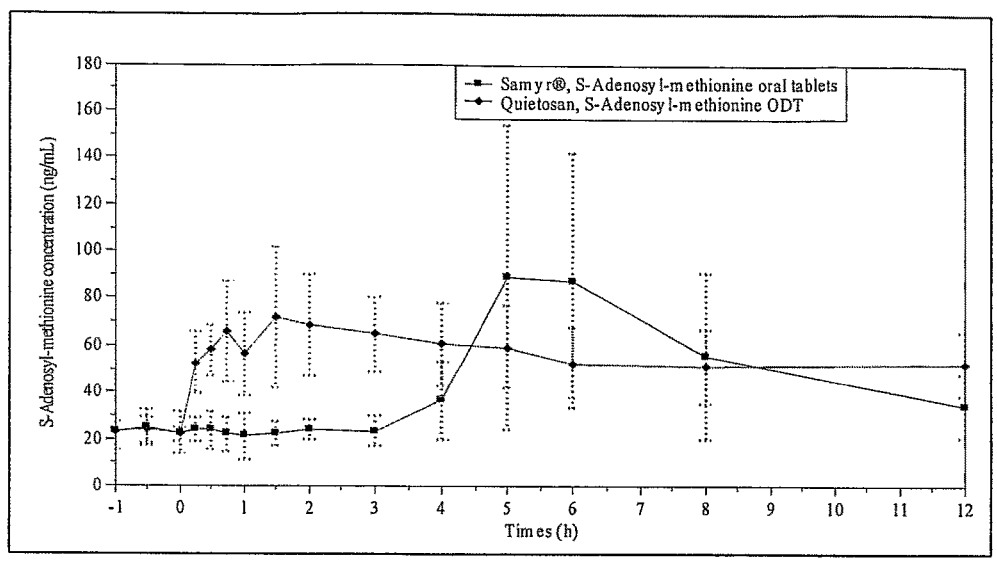

In addition, considering the plasma concentration of SAMe tosylate after 12 hours from intake of the tablet of the invention, as shown in FIG. 2, it is about 30% higher than the base value, while the plasma concentration of SAMe tosylate after 12 hours from the intake of the swallowable gastro-resistant tablet is about 11% higher with respect to the base value.

Analogously, a trial was carried out on two healthy volunteers with respect to the orosoluble and effervescent composition of example 2 of the present invention which showed an intermediate pharmacokinetic behaviour between the orosoluble form tablets of the invention and the swallowable gastro-resistant one available in the market.

The orosoluble and effervescent composition revealed an AUC about 30-40% higher with respect to the swallowable gastro-resistant form and a time of about 1-2 hours.

Thus, the advantage deriving from the compositions based on at least a salt of SAMe in orosoluble and/or effervescent form with high palatability according to the present invention is observable from the data indicated above.

The invention claimed is:

1. Method for obtaining the plasma peak of the S-adenosyl methionine ion within a period of time comprised between 1 and 2 hours characterized by administering a pharmaceutical, dietary and/or nutraceutical orosoluble tablet composition containing at least a salt of S-adenosyl methionine combined with physiologically acceptable excipients wherein said physiologically acceptable excipients comprise light magnesium oxide and at least one fat selected from the group consisting of stearic acid and hydrogenated vegetable oil wherein said tablet is configured for orosolubility.

2. Method according to claim 1, for obtaining the plasma peak of the S-adenosyl methionine ion after about one and a half hours from intake of the composition.

3. A method of treatment of a disease, wherein said method comprises the step of administering an orosoluble tablet containing at least a salt of S-adenosyl methionine combined with physiologically acceptable excipients wherein said physiologically acceptable excipients comprise light magnesium oxide, and at least one fat selected from the group consisting of stearic acid and hydrogenated vegetable oil to treat a disease selected from the group consisting of neuropsychiatric, osteoarticular and hepatic diseases.

4. The method of claim 3, wherein said step of treating a disease comprises treating a disease selected from the group consisting of depression syndromes, anxiety, dementia, alcoholic steatosis, acute hepatitis, chronic hepatitis, alcoholic cirrhosis, post-viral cirrhosis, intrahepatic cholestasis and degenerative skeletal-muscular diseases with mobility disorders.

5. A method of increasing the plasma concentration of the S-adenosyl methionine ion within a patient, wherein said method comprises the step of administering a pharmaceutical, dietary, and/or nutraceutical orosoluble tablet containing at least a salt of S-adenosyl methionine combined with physiologically acceptable excipients wherein said physiologically acceptable excipients comprise light magnesium oxide and at least one fat selected from the group consisting of stearic acid and hydrogenated vegetable oil.

6. The method of claim 5, wherein said method produces a plasma concentration of s-adenosyl methionine at least 40% higher with respect to the base value within a period of time comprising between 1 and 2 hours.

7. The method of claim 5 wherein said method produces a plasma concentration of s-adenosyl methionine at least 50% higher with respect to the base value within a period of time comprising between 1 and 2 hours.

8. The method of claim 5 wherein said method produces a plasma concentration of s-adenosyl methionine at least about 48% higher with respect to the base value after about 1 and a half hours from intake.

* * * * *